United States Patent
Shimokawa et al.

(10) Patent No.: US 6,300,364 B1
(45) Date of Patent: Oct. 9, 2001

(54) MEDICINAL COMPOSITIONS WITH CHOLESTEROL-LOWERING EFFECT

(75) Inventors: Teruhiko Shimokawa; Satomi Nishijima; Koyo Matsuda; Yuichi Iizumi; Seiichi Hashimoto, all of Ibaraki (JP)

(73) Assignee: Yamanouchi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/463,334

(22) PCT Filed: Jul. 22, 1998

(86) PCT No.: PCT/JP98/03266

§ 371 Date: Jan. 24, 2000

§ 102(e) Date: Jan. 24, 2000

(87) PCT Pub. No.: WO99/04815

PCT Pub. Date: Feb. 4, 1999

(30) Foreign Application Priority Data

Jul. 24, 1997 (JP) .................................................. 9-198232

(51) Int. Cl.[7] .......................... A01N 43/38; A01N 43/12; A01K 31/40; C07D 257/04; C07D 403/00

(52) U.S. Cl. .................. 514/415; 514/414; 514/418; 514/419; 514/443; 548/250; 548/252; 548/254; 548/454; 548/506

(58) Field of Search .................. 514/415, 414, 514/418, 419, 443, 469, 510, 513, 515, 529; 548/250, 252, 254, 454, 506, 507

(56) References Cited

U.S. PATENT DOCUMENTS 6,090,839 * 7/2000 Adams et al. ................ 514/415

FOREIGN PATENT DOCUMENTS

| 281 130 | 6/1996 | (CZ) | C07C/49/78 |
|---|---|---|---|
| 61-268657 | 11/1986 | (JP) | C07C/93/20 |
| 62-174057 | 7/1987 | (JP) | C07D/235/28 |
| 2-215717 | 8/1990 | (JP) | A61K/31/41 |
| WO 97/10813 | 3/1997 | (WO) | |
| WO 97/10819 | 3/1997 | (WO) | |

OTHER PUBLICATIONS

Nature, vol. 383, No. 3, p. 450–453 (No Date).
J. Biol. Chem., vol. 275, No. 3, p. 1873–1877 (2000).
Forman, Barry Marc et al., "Hypolipidemic drugs, polyunsaturated fatty acids, and eicosanoids are ligands for peroxisome proliferator–activated receptors α and δ", Proc. Natl. Acad. Sci. USA, Apr. 1997, vol. 94, pp. 4312–4317.
Shimokawa, Teruhiko et al., "Cholesterol–Lowering Effect of YM–16638 in Cynomolgus Monkeys", Drug Development Research, 1996, vol. 38, pp. 86–92.
International Search Report.
Jeffrey M. Peters et al., "Alterations in lipoprotein metabolism in peroxisome proliferator–activated receptor alpha–deficient mice", Journal of Biological Chemistry, vol. 272, No. 43, 1997, pp. 27307–27312.
F.J. Gonzalez, "Recent update on the PPAR alpha–null mouse", Biochimie, vol. 79, 1997, pp 139–144.

* cited by examiner

Primary Examiner—W. Gary Jones
Assistant Examiner—Arun kr. Chakrabarti
(74) Attorney, Agent, or Firm—Sughrue, Mion, Zinn, Macpeak & Seas, PLLC

(57) ABSTRACT

Pharmaceutical compositions having a cholesterol-lowering effect which comprises as the active ingredient a compound having a PPAR (peroxisome proliferator-activated receptor)δ activating effect or a PPARδ- and PPARγ-activating effect or a pharmaceutically acceptable salt thereof; pharmaceutical compositions wherein the cholesterol-lowering effect is an LDL-cholesterol-lowering effect; and a method for identifying a compound having a cholesterol-lowering effect characterized by measuring the PPARδ-activating effect or the PPARδ- and PPARγ-activating effect thereof. Means for Solution: It is found out that a compound exerting an excellent cholesterol-lowering effect on higher animals such as humans and ape has an effect of activating PPARδ or PPARδ and PPARγ. Also, a method for identifying a compound having an excellent cholesterol-lowering effect was found, wherein the desired compound can be quickly and efficiently screened from among a number of compounds by measuring the PPARδ-activating effect or the PPARδ- and PPARγ-activating effect.

4 Claims, No Drawings

SEQUENCE LISTING

<160> NUMBER OF SEQ ID NOS: 6

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 1
ttcccgggga tgtcacacaa tgcaattcgc                              30

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 2
ttggatcctc agtacaaaat gtctctgtag atctc                        35

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 3
ttcccgggca tgtcgcacaa cgctat                                  26

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 4
ttggatcctt agtacatgtc cttgtagatt                              30

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 5
ttcccgggga tgtctcacaa tgccatc                                 27

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 6
ttggatccct aatacaagtc cttgtagat                               29

MEDICINAL COMPOSITIONS WITH CHOLESTEROL-LOWERING EFFECT

TECHNICAL FIELD

This invention relates to: (1) pharmaceutical compositions having a cholesterol-lowering effect which comprises as the active ingredient a compound having a PPARδ-activating effect or a PPARδ- and PPARγ-activating effect, or a pharmaceutically acceptable salt thereof; (2) pharmaceutical compositions wherein the cholesterol-lowering effect is an LDL-cholesterol-lowering effect; (3) pharmaceutical compositions having a cholesterol-lowering effect which comprises as the active ingredient p-[3-(4-acetyl-3-hydroxy-2-propylphenoxy)propoxy]phenylacetic acid or a pharmaceutically acceptable salt thereof; and (4) a method for identifying a compound having a cholesterol-lowering effect characterized by measuring the peroxisome proliferation-activated receptor (PPAR)δ-activating effect or the PPARδ- and PPARγ-activating effect thereof

BACKGROUND ART

An increase in blood lipid level, in particular, LDL (low density lipoprotein)-cholesterol level is considered as one of the important factors causing arteriosclerosis. LDL-cholesterol-lowering agents known hitherto include inhibitors for HMG-CoA (3-hydroxy-3-methylglutaryl coenzyme A) reductase, which is the rate-limiting enzyme in the cholesterol biosynthesis, and inhibitors for the intestinal reabsorption of cholesterol. For example, it is regarded that the mechanism of lowering serum LDL-cholesterol level by the administration of an HMG-COA reductase inhibitor is based on a decrease in the intracellular cholesterol and its metabolite due to the inhibition of the biosynthesis of cholesterol mainly in the liver and acceleration of the LDL receptor expression accompanying therewith (J. Lipid Res., 33, p.1569–1582, 1992).

In the phase I clinical test on simvastatin which is one of the HMG-COA reductase inhibitors, the serum cholesterol level of normal subjects showed a decrease of about 20% about 1 week after the initiation of the administration but no continuous decrease could be expected any more even though the administration was continued. It is also reported that the decrease was about 20% in a patient with hyperlipemia showing a total serum cholesterol level of 220 mg/dl or above (A. Yamamoto et al., Rinsho Iyaku (Clinical Medicine), 4(3), p.409, 1988).

On the other hand, a compound YM-16638 disclosed in an examined Japanese patent publication 63-35626, which inherently has a potent antagonism to SRS-A (slow reacting substance of anaphylaxis), is known as being useful as a preventive and a remedy for various allergic diseases (for example, bronchial asthma, urticaria), ischemic heart and brain diseases, inflammation, etc. and an antiulcer agent (Arzneim.-Forsch. Drug Res., 38(1), p.682–685, 1988; Prostaglandins Leukotrienes and Essential Fatty Acids, 36, p.43–47, 1989).

In a clinical test on this compound as an antiulcer/antiasthmatic agent, it was unexpectedly found out that this compound also showed a potent serum cholesterol-lowering effect in humans. It was also confirmed that a similar effect was observed in animal experiments (Drug Dev. Res., 38, p.86–92, 1996; an unexamined published Japanese patent application 2-215717). The above-described decrease in serum cholesterol level in the normal subjects ranged from about 26% (administration dose: 60 mg) to 41% (administration dose: 120 mg) (Drug Dev. Res., 38, p.86–92, 1996). In an initial phase II clinical test, about 80% of subjects showed a decrease of about 20 to 50%. This potent serum cholesterol-lowering effect on humans is caused not by a decrease in HDL (high density lipoprotein)-cholesterol but a significant decrease in the LDL-cholesterol apoprotein B. It is known that, on the other hand, the compound has only a weak effect of lowering serum triglyceride level (Drugs, 53(2), p.299–336, 1997).

As the results of studies on the function mechanism of the serum cholesterol-lowering effect of YM-16638, it has been clarified so far that this compound has effects of inhibiting the biosynthesis of cholesterol in the liver (Br. J. Pharmacol., 118, p.174–178, 1996), activating LDL receptor and elevating the LDL receptor gene expression level in the liver (Drug. Dev. Res., 38, p.86–92, 1996). However, the further detailed function mechanism of the compound YM-16638 achieving these effects is still unknown.

In the course of recent studies on the mechanism of the differentiation and proliferation of adipose cells, there has been proved the presence of PPAR (peroxisome proliferator-activated receptor) which is a nuclear receptor (Nature, 347, p.645–650, 1990). It has been clarified hitherto that PPAR can be roughly classified into 3 subtypes respectively called PPARα, PPARδ and PPARγ (Proc. Natl. Acad. Sci. USA, 91, p.7355–7359, 1994; Tanpakushitsu Kakusan Koso (Protein, Nucleic acid and Enzyme), 40(13), p.50–55, 1995). Furthermore, the activation of these PPAR subtypes and lipid-lowering effects of various compounds has been reported. For example, it is known that thiazolidinedione compounds, which are employed as remedies for diabetes, serve as PPARγ ligands and significantly lower the serum triglyceride level but do not lower the serum cholesterol level in human (Diabetes, 46, p.433–439, 1997; Diabetes Care, 19(2), p.151–156, 1996, 15(2), p.193–203; Diabetologia, 39, p.701–709, 1996 (Reference 1)). On the other hand, it is known that drugs of the fibrate type, which have been employed as lipid-lowering agents for a long time, serve as PPARα ligands and generally exhibit a potent effect of lowering serum triacylglycerol level in clinics (Proc. Natl. Acad. Sci. USA, 94, p.4312–4317, 1997; Drugs, 40(2), p.260–290, 1990 (Reference 2)).

Similar to these fibrate drugs, Wy 14,643 (prinixic acid) is known as a ligand specific to PPARα (EMBO J. 11, p.433–439, 1992; Arch. Biochem. Biophys., 228(1), p.185–196, 1984 (Reference 3)). However, there has never been reported the lipid-lowering effect of this compound on higher animals. Although it has been proved that prostacyclin (PGI$_2$) employed as an antithrombotic agent, etc. activates neither PPARα nor PPARδ (Proc. Natl. Acad. Sci. USA, 94, p.4312–4317, 1997), it is reported that carbaprostacyclin (cPGI$_2$), which is a derivative of PGI$_2$, has activities of both of PPARα and PPARδ ligands. However, no detailed report has been made so far on the lipid lowering effect of this compound (J. Bio. Chem., 272(9), p.5367–5370, 1997; Proc. Natl. Acad. Sci. USA, 94, p.4312–4317, 1997 (Reference 4)).

On the other hand, Great Britain Published Patent Application GB 2292885 claims a drug for hyperlipemia wherein a substance activating NUC1 (human PPARδ) receptor is administered. However, the description on the regulation of enzyme level relating to the fatty acid oxidation disclosed in the specification of this reference relates to the metabolism of triglycerides. Namely, this reference neither discloses nor suggests any cholesterol-lowering effect.

That is, it has never been confirmed hitherto which subtype of PPAR participates in the serum cholesterol-lowering effect, though a number of findings have been made as described above.

It is expected that cholesterol-lowering agents based on the novel function mechanism in which a PPAR subtype participates would be superior in efficaciousness to the existing drugs. However, the above-described function mechanism has never been clarified hitherto and, therefore, no satisfactory drug therefor has been found out so far. Therefore, it has been keenly demanded to develop a pharmaceutically satisfactory drug having a clarified function mechanism in which a PPAR subtype participates and exerting an excellent cholesterol-lowering effect.

Disclosure of the Invention

The present inventors conducted extensive studies on the cholesterol-lowering function mechanism of the above-described compound YM-16638. As a result, they found out for the first time that this compound has an effect of activating PPARδ and PPARγ. Based on this finding and the conventional report that thiazolidinedione compounds, which are PPARγ ligands, do not lower the serum cholesterol level, the present inventors considered that PPARδ might mainly participate in the cholesterol-lowering effect as described above. Thus, they conducted further studies on compounds having a PPARδ-activating effect. Namely, they searched for compounds having the PPARδ-activating effect by using a method characterized by measuring the PPARδ-activating effect or the PPARδ- and PPARγ-activating effect. As a result, they found out that p-[3-(4-acetyl-3-hydroxy-2-propylphenoxy)propoxy]phenylacetic acid disclosed in Czech Patent CZ 281130 as a compound having anti-inflammatory and antiasthmatic effects showed a PPARδ- and PPARγ-activating effect and, unexpectedly, exhibited excellent effects of lowering serum-cholesterol and LDL-cholesterol in experiments with the use of higher animals, similar to YM-16638. Thus, they have completed the present invention based on these findings.

Accordingly, the present invention relates to pharmaceutical compositions having a cholesterol-lowering effect which contain as the active ingredient a compound having a PPARδ-activating effect or a PPARδ- and PPARγ-activating effect or a pharmaceutically acceptable salt thereof.

The present invention further relates to pharmaceutical compositions wherein the above cholesterol-lowering effect is an LDL-cholesterol-lowering effect.

The present invention furthermore relates to pharmaceutical compositions having a cholesterol-lowering effect which comprises as the active ingredient p-[3-(4-acetyl-3-hydroxy-2-propylphenoxy)propoxy]phenylacetic acid or a pharmaceutically acceptable salt thereof.

The present invention furthermore relates to a method for identifying a compound having a cholesterol-lowering effect characterized by measuring the PPARδ-activating effect or the PPARδ- and PPARγ-activating effect thereof.

Now, the present invention will be described in greater detail.

The expression "peroxisome proliferator-activated receptor (PPAR) activating effect" as used herein means the whole effect of the early stage, namely, a compound directly binds to the ligand-binding site of the receptor and acts thereon or indirectly acts thereon so that the function is expressed by the ligand-binding receptor. When the data determined by measuring the receptor-activating effect of a certain compound are statistically judged as being significantly different from the control data determined in the absence of the compound (under the addition of dimethyl sulfoxide employed as the solvent herein), the compound is referred to as "having the activating effect".

The term "cholesterol-lowering effect" as used herein means an effect of significantly lowering the serum cholesterol level in a pathologic state with the need for some therapeutic treatment (usually 220 mg or more). Pharmaceutical compositions having the cholesterol-lowering effect are useful in preventing and treating various diseases caused by an increase in the serum cholesterol level.

The "compound having a PPARδ-activating effect or a PPARδ- and PPARγ-activating effect" which is the active ingredient of the pharmaceutical compositions having a cholesterol-lowering effect according to the present invention involves any compounds, both known ones and novel ones, having a PPARδ-activating effect or a PPARδ- and PPARγ-activating effect, for example, those selected by the method for identifying a compound having a cholesterol-lowering effect from among various known compounds registered in Chemical File and those newly synthesized by using various substituents attached to the mother nuclei of the compounds thus selected.

The term "pharmaceutically acceptable salts" as used herein means biologically nontoxic salts formed by the corresponding compound with an acid or a base.

Illustrative examples thereof include acid addition salts with inorganic or organic acids and salts with inorganic or organic bases. Examples of these pharmaceutically acceptable salts include acid addition salts with mineral acids (e.g., hydrochloric acid, hydrobromic acid, hydroiodic acid, sulfuric acid, nitric acid, phosphoric acid, etc.), organic acids (e.g., formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, benzenesulfonic acid, toluenesulfonic acid, etc.) and acidic amino acids (e.g., aspartic acid, glutamic acid, etc.), inorganic bases (e.g., sodium, potassium, magnesium, calcium, aluminum, lithium, etc.), organic bases (e.g., methylamine, ethylamine, ethanolamine, etc.), basic amino acids (e.g., lysine, ornithine, etc.) and ammonium salts.

Further, the compound of the present invention sometimes forms hydrates, solvates with ethanol, etc. or polymorphic crystal forms. The present invention involves within the scope thereof all of these hydrates, solvates and polymorphic crystal forms, either in a separated state or as a mixture thereof.

The method for identifying a compound having a cholesterol-lowering effect according to the present invention is characterized by measuring the PPARδ-activating effect or the PPARδ- and PPARγ-activating effect thereof. That is, the present invention provides a method for confirming the PPARδ-activating effect or the PPARδ- and PPARγ-activating effect of a compound or selecting a compound having a cholesterol-lowering effect. This method involves the following steps: (a) construction of an expression cassette encoding a functional fragment of the PPARδ or PPARγ receptor; (b) formation of a construction wherein one or more response elements to a functional protein fragment binding to the above-described receptor fragment are ligated to a reporter gene; (c) cotransfection into a host by using this construction; (d) addition of test compounds; (e) measurement of the expression of the reporter gene; and (f) selection of a compound having a PPARδ-activating effect or a PPARδ- and PPARγ-activating effect via comparison of the test compounds with a control. By using this method, a number of compounds can be quickly and efficiently assayed, thereby effecting random screening.

The above-described steps (a) and (b) have been established recently as a system for evaluating nuclear receptor ligands. Speaking in greater detail, it is a reporter system by taking advantage of the binding of a regulatory factor of galactose metabolism enzyme regulatory proteins GAL4 (Gall (galactokinase), GAL7 (α-D-galactose-1-phosphate uridyltransferase), GAL10 (uridine diphosphoglucose-4-epimerase)) expressed in a yeast (Saccharomyces cerevisiae) to its responsive sequence $UAS_G$ (galactose upstream activating region) (Cell, 40, p.767–774, 1985; 52, p.161–167, 1988; 52, p.169–178, 1988; 54, p.199–207, 1988). In addition to the reporter system described in Example 1 hereinafter with the use of the ability of the yeast GAL4 protein to bind to DNA (J. Biol. Chem., 270(2), p.12953–12956, 1995), it is also possible to use a reporter system with the use of a responsive sequence (peroxisome proliferator responsive element, PPRE) to which PPAR DNA-binding domain binds (Proc. Natl. Acad. Sci. USA, 94, p.4312–4317, 1997; 91, p.7355–7359, 1994; J. Biol. Chem., 268(8), p.5530–5534, 1993), a reporter system with the use of a bacteria tetracycline operon (J. Biol. Chem., 270(41), p.23975–23983, 1995), etc.

The basic techniques relating to the gene manipulation required in the construction of a vector as described in Example 1 can be performed by reference to Basic Methods in Molecular Biology, $2^{nd}$ Edition (Leonard G. Davis, W. Michael Kuehl, James F. Battey, Prentice-Hall International Inc., 1994) and "Bio-Jikken Illustrated (Illustrated Biological Experiments) ② Idenshi Kaiseki no Kiso (Basic Gene Analysis)" (Hiroki Nakayama and Keito Nishikata, extra number of Saibo Kogaku (Cell Engineering), Shujun-sha, 1995).

The gene expression vector to be used in the step (a) of the method according to the present invention is a marketed vector which already contains a gene encoding the DNA-binding domain of GAL4 protein (GAL4-DBD), i.e., pGBT9 DNA-Binding Domain Vector (vector size: 5.5 kb, having the GAL4-DBD region and an ampicillin resistance gene $Amp^R$ sequence therein, manufactured by Clontech). This vector is sufficiently advantageous in that a chimeric protein, which is expressed in cells by transferring the ligand-binding domain of the target nuclear receptor into the multiple cloning site (MCS) in the vicinity of the GAL4-DBD region of the vector, is usable as a sensor in the identification method according to the present invention. As a substitute for pGBT9, use may be made of another product pAS2 DNA-Binding Domain Vector (manufactured by Clontech). Also, a method described in a reference (Cell, 52, p.169–178 (1988)) or modifications thereof are usable for the construction of the vector.

A fused vector composed of a responsive element to the activated chimeric protein with a reporter gene to be used in the step (b) is obtained by constructing a known responsive element and transferring it into an expression vector containing luciferase gene (PICA GENE VECTOR 2 (PGV-B2), manufactured by Toyo Ink Mfg.). It is usually inserted via a short fragment carrying an appropriate restriction enzyme site. Namely, the fused vector is synthesized in a conventional manner by, for example, cleaving the reporter gene with an appropriate restriction enzyme and then inserting the responsive element in the vicinity of the reporter gene. The responsive element having an adequate end to be used therein is constructed on a DNA synthesizer.

Although a known responsive element can be constructed on a DNA synthesizer as described above, it is also possible to use one which has been already integrated into an appropriate marketed vector, for example, pG5CAT reporter plasmid (manufactured by Clontech). It is desirable to select and use a responsive element showing a good response in the host to be used in the identification of the target compound as will be described hereinafter.

It is preferable to select appropriate promoter and terminator sequences, which are preferably active in the host as will be described hereinafter, well known in the art. These sequences can bind to structural genes, arbitrary marker groups and other elements convenient for standard gene engineering techniques.

Examples of the preferable host cells usable in the expression of the construction formed in the step (c) of the method for identifying a compound having a cholesterol-lowering effect according to the present invention involve cells of bacteria, fungi such as yeasts, insects and mammals. Typical examples thereof are HepG2, NIH-3T3, COS-1, COS-7, U-937, CV-1, KI-293, etc. Among all, HepG2, CV-1 and NIH-3T3 are preferable therefor. Gene transfer experiments with the use of these cells may be carried out under such conditions that little cytotoxicity is induced and the target gene is transferred in a large amount and hardly degraded. Namely, the gene transfer method is not restricted to the one with the use of lipofectamine as employed in Example 1.

In the step (d), a known compound registered in Chemical File or a newly synthesized one is diluted at an appropriate ratio and then added to the medium of the cells into which the genes have been transferred, followed by the measurement of the step (e). This treatment may be performed as, for example, a high through put screening system with the use of a 96-well plate.

In the step (d), the compound is dissolved in an appropriate solvent and then added to the medium of the cells. The incubation is carried out under necessary and sufficient conditions for the measurement of the two genes, which have been transferred into the cells, and the substances acting thereon on the basis of the reporter activity. When the compound cannot permeate through cell membrane, it is possible to add an appropriate carrier or to use a cell-free system.

In the present invention, the expression of the reporter gene can be determined on the basis of the transcription level or the translation level, for example, by measuring the protein product, enzyme activity or cell proliferation.

As the indication to be measured in the step (e), there have been known in the art appropriate reporter genes, for example, firefly luciferase (luc, PGV, manufactured by Pica Gene), sea pansy luciferase (luc, pRL, manufactured by Pica Gene), bacterial hybrid luciferase (luXAB), chloramphenicol acetyltransferase (CAT) and β-Dgalactosidase (lacZ).

In the step (f), the solvent of the test compound is used as a control and the reporter gene expression in the step (e) is measured. Then, the relative ligand activity of the test compound is calculated by referring the activity of the control as to 1.0. Thus a compound showing a significant effect of activating PPARδ or PPARδ and PPARγ can be selected.

Industrial Applicability

The pharmaceutical compositions provided by the present invention are characterized by having a novel function mechanism, namely, an effect of activating PPARδ, which is a peroxisome proliferator-activated receptor subtype, or an effect of activating PPARδ and PPARγ. These pharmaceutical compositions are expected as being much superior to the conventional drugs particularly in the pharmaceutical effects on higher organisms including humans and ape.

p-[3-(4-Acetyl-3-hydroxy-2-propylphenoxy)propoxy] phenylacetic acid according to the present invention occurs as various isomers such as ketoenol tautomers based on the hydroxyl group, etc. in its chemical structure. The present invention involves within the scope thereof all of these isomers which are either isolated individually or exist as mixtures thereof.

The compound of the present invention further forms salts with bases. Examples of such salts include those formed with inorganic bases (e.g., sodium, potassium, magnesium, calcium, aluminum, etc.), organic bases (e.g., methylamine, ethylamine, ethanolamine, lysine, arginine, ornithine, etc.) and ammonium salts. Furthermore, the compound of the present invention is sometimes obtained as hydrates, solvates with ethanol, etc. or polymorphic crystal forms showing various crystalline forms depending on the physicochemical properties thereof or production conditions. The present invention also involves within the scope thereof all of these hydrates, solvates with ethanol, etc. and various crystal forms.

The compound according to the present invention can be produced by the process as will be described in Production Example 1 or modifications thereof known by those skilled in the art. It is isolated either as a free compound or as a salt thereof. A salt of the compound of the present invention can be produced by subjecting the compound of the present invention in the state of a free acid or a free base to a conventional salt-forming reaction. The obtained product is isolated and purified by applying common chemical procedures such as extraction, concentration, distillation, crystallization, filtration, recrystallization or various chromatographic techniques. Various isomers of the compound of the present invention can be isolated form each other by a conventional method with the use of a difference in physicochemical properties between the isomers.

Effects of the Invention

The pharmaceutical compositions having a cholesterol-lowering effect according to the present invention show an excellent effect of lowering serum cholesterol, in particular, LDL-cholesterol particularly in higher animals such as humans and ape based on novel function mechanism of activating PPARδ or activating PPARδ and PPARγ.

It has been confirmed that the method for identifying a compound having a cholesterol-lowering effect according to the present invention is useful in selecting a compound having an excellent cholesterol-lowering effect in practice. Namely, this method is highly useful in quickly and efficiently screening and selecting a target compound having a cholesterol-lowering effect from among a number of compounds.

Accordingly, the pharmaceutical compositions of the present invention are highly useful in preventing and treating, based on the above-described effects, various diseases caused by an increase in the serum cholesterol, in particular, an increase in the LDL-cholesterol, namely, hypercholesterolemia, hyperlipemia, xanthoma, arteriosclerosis or various diseases caused by arteriosclerosis (ischemic heart diseases such as angina pectoris and myocardial infarct based on circulatory arteriosclerosis, cerebrovascular failures such as cerebral infarction and cerebral hemorrhage due to cerebrovascular hardening, optic nerve atrophy and hydrocephay caused by mechanical oppression of hardened cerebral artery, sclerotic kidney based on hardening of renal artery, aneurysm and obstructive arteriosclerosis due to narrowing of aorta or peripheral artery, etc.).

The preparation according to the present invention containing one or more active ingredients selected from among a compound having an effect of activating PPARδ or an effect of activating PPARδ and PPARγ or its salts is prepared by using commonly employed pharmaceutical carriers, fillers and other additives. It may be processed into any form suitable for oral administration (tablets, pills, capsules, granules, powders, solution, etc.) or parenteral administration (e.g., intravenous or intramuscular injections, suppositories, percutaneous preparations, etc.). The administration dose is appropriately determined case by case depending on the symptom, age, sex, etc. of the patient. In the case of oral administration, the daily dose to an adult usually ranges from 1 to 500 mg. In the case of parenteral administration, the daily dose to an adult usually ranges from 0.1 to 50 mg. Administration is made once or 2 to 4 times per day.

Examples of solid preparations for oral administration according to the present invention include tablets, powders and granules. In such a solid preparation, at least one active substance is mixed with at least one inactive diluent, for example, lactose, mannitol, glucose, hydroxypropyl cellulose, microcrystalline cellulose, starch, polyvinylpyrrolidone, metasilicic acid or magnesium aluminate. The composition may further contain additives other than the inactive diluent, for example, lubricant (magnesium stearate, etc.), disintegrating agents (cellulose, calcium glycolate, etc.), stabilizers (lactose, etc.), dissolution aids (glutamic acid, aspartic acid, etc.) in a conventional manner. Tablets and pills may be sugar-coated with sucrose, gelatin, hydroxypropyl cellulose, hydroxypropylmethyl cellulose phthalate, etc. or coated with an enteric film, if necessary.

Examples of liquid compositions for oral administration include pharmaceutically acceptable emulsions, solutions, suspensions, syrups and elixirs. Such a liquid composition contains inactive diluents commonly employed in the art, for example, purified water or ethanol. In addition to the inactive diluents, it may further contain humectants, auxiliary agents (suspending agents, etc.), sweeteners, flavors, aromas and preservatives.

Examples of injections for parenteral administration include sterile aqueous or nonaqueous solutions, suspensions and emulsions. Aqueous solutions and suspensions contain, for example, distilled water for injection or physiological saline. Nonaqueous solutions and suspensions contain, for example, propylene glycol, polyethylene glycol, vegetable oils (e.g., olive oil, etc.), alcohols (e.g., ethanol, etc.) or polysorbate™ 80. Such a composition may further contain auxiliary agents such as preservatives, humectants, emulsifiers, dispersing agents, stabilizers (e.g., lactose, etc.) and dissolution aids (e.g., glutamic acid, aspartic acid, etc.). These compositions are sterilized by, for example, filtering through a bacterial retention filter, adding bactericides, or irradiating. It is also possible to produce a sterile solid composition which is dissolved in sterile water or a sterile injection solvent before use.

Best Mode for the Embodiment of the Invention:

The method for identifying a compound having a cholesterol-lowering effect, cholesterol-lowering preparations and compounds according to the present invention will be described in greater detail by reference to the following Examples.

EXAMPLE 1

Method for identifying compound having cholesterol-lowering effect (1) Construction of activation vectors To identify a compound having a PPARδ and PPARγ ligand effect, fused gene expression vectors of the DNA-binding domain (GAL4-DNA bindgn domain, GAL4-DBD) of a yeast transcription activated protein and the PPAR ligand binding domains (LBDs) were constructed. Three activation vectors thus constructed were named GAL-PPARα, GAL-PPARδ and GAL-PPARγ respectively. The construction process involved the following steps: i) cloning of PPAR-LBDs; ii) construction of fused vectors by transferring a GAL4-DBD gene-containing vector; and iii) subcloning into an expression vector (J. Biol. Chem., 270(22), p.12953–12956, 1995; Cell, 83, p.803–812, 1995).

i) Ligand binding domains (PPAR-LBDs) of mouse peroxisome-proliferator-activated receptors (mPPARα, mPPARδ and mPPARγ) were each amplified by PCR (polymerase chain reaction). As a template employed in the amplification, total RNA was prepared from a fat tissue around mouse epididymis with the use of a total RNA extracting reagent Isogen (manufactured by Nippon Gene) in accordance with the attached manufacturer's instruction. Base sequences of primers synthesized for cloning genes respectively encoding the ligand binding domains of the PPAR subtypes were as follows: mPPARα ($Gly^{165}$-$Tyr^{467}$) 5'-TTC CCG GGG ATG TCA CAC AAT GCA ATT CGC-3' (SEQ ID NO:1) and 5'-TTG GAT CCT CAG TAC AAA ATG TCT CTG TAG ATC TC-3' (SEQ ID NO;2), mPPARδ ($Met^{137}$-$Tyr^{439}$); 5'-TTC CCG GGC ATG TCG CAC AAC GCT AT-3' (SEQ ID NO:3) and 5'-TTG GAT CCT TAG TAC ATG TCC TTG TAG ATT-3' (SEQ ID NO;4), mPPARγ ($Gly^{172}$-$Tyr^{474}$); 5'-TTC CCG GGG ATG TCT CAC AAT GCC ATC-3' (SEQ ID NO:5) and 5'-TTG GAT CCC TAA TAC AAG TCC TTG TAG AT-3' (SEQ ID NO:6). PCR was performed by using GeneAmp PCR System Model 9600.

ii) Into one side of each primer thus synthesized, a recognition sequence of a restriction enzyme SmaI or BamHI had been preliminarily inserted so that the primer could be cleaved with the restriction enzyme. After the amplification, the PCR fragment was ligated with pGBT9 DNA-Binding Domain Vector (5.5 kb, having the GAL4-DBD domain and an ampicillin resistance gene $Amp^R$ sequence, manufactured by Clontech) and the vector thus formed was named pGBT9-PPAR-LBD.

iii) A fused gene domain (GAL4-DBD+PPAR-LBD) wherein GAL4-DBD contained in pGBT9-PPAR-LBD was legated to PPARLBD was excised by using HindIII/SalI and transferred into the multiple cloning site (MCS) of an expression vector pZeoSV (3.5 kb, having zeocin resistance gene $Zeo^R$ sequence, manufactured by Clontech) by using HindIII/Xhol. The thus obtained chimeric expression vectors of GAL4-DBD ad PPAR-LBD were named respectively GAL-PPARα, GAL-PPARδ and GAL-PPARγ.

(2) Construction of reporter vector

A reporter gene with the expression of luciferase as an indication (hereinafter referred to as RE-LUC) was constructed by the following two steps: i) formation of a GAL4 responsive sequence; and ii) subcloning into a luciferase-expression vector (J. Biol. Chem., 270(22), p.12953–12956, 1995; and Cell, 83, p.803–812, 1995).

i) DNA sequences were synthesized by using a DNA synthesizer (Beckman DNA Synthesizer oligo1000M, manufactured by Beckman) by repeating the GAL4-DBD binding sequence (GAL4 responsive element, RE or $UAS_G$) once (RE×1) or thrice (RE×3). Then appropriate restriction enzyme cites were introduced into both ends and these sequences were ligated together to give a 4-repetition sequence fragment (RE×4). Further, an 8-repetition sequence fragment (RE×8) was formed by using the same.

ii) A DNA sequence wherein TATA box was ligated to the above GAL4 responsive sequence (RE×8) was formed by PCR and then inserted into the 5'-side upstream of the luciferase gene sequence (RE-LUC) in a vector for luciferae assay system (Pica Gene Vector-2, (PGV-B2), Toyo Ink Mfg.). After preparing samples by using a sequencing kit (PRISM™ Ready Reaction DyeDeoxy™ Terminator Cycle Sequencing Kit, manufactured by Applied Biosystems), the base sequence of the inserted region containing RE×8 and TATA box of RE-LUC was confirmed by using a sequencer (ABI 373A DNA sequencer, manufactured by Applied Biosystems). RE-LUC containing RE×8 was transferred into cells together with GAL-PPARγ. Then CS-045 (troglitazone), i.e., the ligand of PPARγ was added. As a result, RE×8 showed a stronger ligand response (luciferase activity) than any other sequences (RE×2, ×3, ×4, ×5, ×6 or ×10). Thus, RE×8 was employed in the evaluation performed herein.

(3) Measurement of activities of PPARα, PPARδ and PPARγ

By using the activation vectors and reporter vectors constructed in the above (1) and (2), the PPAR activation effect of a compound was measured by a method involving the following three steps: i) Cotransfection of construction into a host; ii) treatment of cells by adding the compound; and iii) assay of the reporter gene expression level.

i) Cotransfection of construction into host

HepG2 cells (American Type Culture Collection, Maryland, USA) was inoculated into a collagen type IV treated 96-well plate (manufactured by Iwaki) at a cell density of $1×10^4$/well and incubated for 2 days in the presence of Dulbecco's modified Eagle medium containing 10% of fetal calf serum (FCS) (200 μl/well, FCS-DMEM (GIBCO BRL)). Next, the cells were washed with 100 μl/well of a cell incubation medium (OPTI-MEM I Reduced Serum Medium, manufactured by GIBCO BRL) maintained at 37° C. Subsequently, a DNA-containing solution (containing the following substances per well (corresponding to 50 μl): 0.01 μg of GAL-PPARα, PPARδ or PPARγ, 0.1 μg of a luciferase vector RE-LUC, 0.02 μg of an eucaryotic cell expression vector pCH110 (vector for β-galactosidase expression (for correcting gene transfer efficiency) manufactured by Pharmacia Biotech) and 1 μl of LipofectAMINE (GIBCO BRL); dissolved in OPTI-MEM by stirring at room temperature for 15 minutes) was added and incubation was carried out at 37° C. for 3 hours.

ii) Treatment of cell by adding compound

The cells were washed twice with 100 μl portions of 10% FCS-DMEM and the incubation medium was replaced by 200 μl of 10% FCS-DMEM containing the test compound ($10^{-4}$ M, dissolved in 5% dimethyl sulfoxide (DMSO)). Then incubation was continued at 37° C. for 48 hours.

iii) Assay of reporter gene expression level

After removing the medium, 100 μl of a solubilizing buffer for assaying luciferase activity (diluted 1-fold, manufactured by Pica Gene) was added. After allowing to stand at room temperature for 15 to 30 minutes, a 20 μl portion thereof was pipetted into another assay plate and 100 μl of a luciferase substrate solution (manufactured by Pica Gene) was added thereto. Next, the luminous intensity (luciferase activity) was measured for 10 seconds by using a chemical luminous meter (Model AB-2100, manufactured by Atto). Simultaneously with the addition of the luciferase gene, the activity expression dose of the β-galactosidase expression gene having been transferred into the cells was measured. Then the variation in the luciferase activity due to the addition of the compound was corrected by using the transfection efficiency of the transferred gene. The β-galactosidase activity was measured in accordance with the manual available from Promega (Methods Enzymol., 152, p.704–720, 1987; Biotechniques, 7, p.576, 1989).

20 μl of a solubilized sample was pipetted into another 96-well plate. After adding thereto 100 μg of an ONPG solution (o-nitrophenyl-β-D-galactopyranoside, manufactured by Promega), incubation was performed at 37° C. for 90 minutes. Then 50 μl of a reaction stopper (1 M solution of sodium carbonate, manufactured by Promega) was added and the absorbance at 415 nm was measured at room temperature. By referring the luciferase activity of cells treated exclusively with dimethylsulfonyl oxide (DMSO, 0.5%) employed as the solvent as to 1.0 (control activity), the relative ligand activity was calculated (Table 1).

As a result, it has been confirmed that YM-16638 and the compound of Production Example 1 have each an effect of activating PPARδ and PPARγ.

TABLE 1

| Test compound | Relative activity (control = 1) | | |
| --- | --- | --- | --- |
| | PPARα | PPARδ | PPARγ |
| YM-16638 | 1.0 | 46.2*** | 2.5* |
| Production Ex. 1 | 0.6 | 83.5*** | 10.3** |
| Comparative compound | | | |
| Pioglitazone[1] | 1.5 | 1.4 | 20.6*** |
| Clofibrate[2] | 2.2* | 1.3 | 0.9 |
| Wy 14,643[3] | 25.0*** | 1.5 | 1.8 |
| cPGI$_2$[4] | 15.2* | 34.0** | 1.6 |

Calibration on statistically significant difference:
 (Dunnett type t-test: two-way Dunnett-test):
 *) $p<0.05$,  $p<0.001$, * $p<0.0001$.
 1) Compound described in Reference 1 cited above.
 2) Compound described in Reference 2 cited above.
 3) Compound described in Reference 3 cited above.
 4) Compound described in Reference 4 cited above.

EXAMPLE 2

Test for evaluating cholesterol-lowering effect by using rhesus monkey:

A test for evaluating cholesterol-lowering effect was performed by using rhesus monkeys in accordance with a method described in Br. J. Pharmacol., 118, p.174–178, 1996.

i) Male rhesus monkeys weighing about 4.5 to 5 kg (Purchased from Hamri) were fed by giving twice a day 50 g/day of a solid feed, which had been prepared by adding 50 ml of water and vitamin C (5 mg/kg/day, manufactured by Sigma) to 50 g of Purina powdery feed (Code #5408, manufactured by Oriental Yeast) and solidifying the mixture, and about 100 g of banana. Then it was confirmed that the animals fed under the above conditions showed no significant variation in body weight.

ii) The monkeys having been accustomed to the control feed were divided into a control group having 4 animals and test groups each having 3 animals. The animals of the test group were fed with the control feed. On the other hand, the animals of one test group were fed with a composition feed containing 30 mg/kg/day of YM-16683, while those of the other test group were fed with a composition feed containing 30 mg/kg/day of the compound of Production Example 1, each twice a day. To avoid unfinished feeding, banana was given to the animals after taking 50 g of each feed.

iii) The groups were fed with respective feeds for 2 weeks. About 16 hours before the day before the final administration, the animals were fasted and the blood samples were collected from thigh. After measuring body weight, blood collection was performed twice, i.e., before and after the administration of the test compound. Each blood sample thus collected was heparinized and serum was separated therefrom. Next, the total cholesterol level (TC) and LDL-cholesterol level (LDL-C) were measured by the enzymatic method with the use of an automatic analyzer (Model 736–10, Hitachi) (Table 2).

Decrease was calculated by comparing the data before the administration.

TABLE 2

Cholesterol-lowering effect on rhesus monkey

| | Decrease in TC | Decrease in LDL-C |
| --- | --- | --- |
| YM-16638 group (n = 3) | 33%* | 14%* |
| Production Example 1 group (n = 4) | 29%* | 34%* |

Calibration on statistically significant difference:
 (Student's t-test:*) $p<0.05$).

As a result, it has been confirmed that YM-16638 and the compound of Production Example 1 show each an excellent effect of lowering serum total cholesterol level, in particular, LDL-cholesterol level.

Production Example 1

5.00 g of methyl 4-hydroxyphenylacetate, 12.15 g of 1,3-dibromopropane and 8.32 g of potassium carbonate were stirred in 30 ml of N,N-dimethylformamide at room temperature over 3 nights. After adding 200 ml of ice-water, the mixture was extracted with ethyl acetate (200 ml×1). The organic layer was washed with water (150 ml×1) and dried over anhydrous magnesium sulfate. After filtering, the filtrate was concentrated to give 8.12 g of a residue. Then, 2.87 g of this residue, 1.94 g of 2-propyl-3-hydroxy-4-acetylphenol and 2.76 g of potassium carbonate were stirred in 30 ml of N,N-dimethylformamide at room temperature overnight. After adding 200 ml of ice-water, the mixture was extracted with ethyl acetate (200 ml×1). The organic layer was washed with water (200 ml×1) and dried over anhydrous magnesium sulfate. After filtering, the filtrate was concentrated to give 4.30 g of a residue. Next, this residue was subjected to silica gel chromatography (Merck, Kieselgel 60) and 1.63 g of a precursor (RF=0.75, TLC plate: Merck DC-Fertigplatten Kieselgel 60 F254, developing solvent: chloroform) was obtained from a chloroform eluate. Then, 1.63 g of this precursor was heated under reflux in 40 ml of methanol and 20.4 ml of a 1 N aqueous solution of sodium hydroxide. After cooling by allowing to stand, 40 ml of a 1 N aqueous solution of hydrochloric acid was further added thereto. The crystals thus precipitated were taken up by filtration, washed with methanol/water and then dried under reduced pressure to give 1.13 g of p-[3-(4-acetyl-3-hydroxy-2-propylphenoxy)propoxy]phenylacetic acid.

Melting point: 106–108° C.

Elemental analysis (as $C_{22}H_{26}O_6$):

| | C (%) | H (%) |
| --- | --- | --- |
| calcd. | 68.38 | 6.78 |
| found | 68.35 | 6.84. |

IR absorption spectrum ν max(KBr)cm$^{-1}$:

2968, 1700, 1638, 1586, 1520, 1504, 1472, 1420, 1378, 1274, 1250, 1126, 1066, 814 and 790.

What is claimed is:

1. A pharmaceutical composition having a cholesterol-lowering effect which comprises as the active ingredient a compound having an effect of activating peroxisome proliferator-activated receptor (PPAR) δ by directly binding thereto or an effect of activating PPAR δ and PPAR γ by directly binding thereto or a pharmaceutically acceptable salt thereof.

2. The pharmaceutical composition as claimed in claim 1, wherein said cholesterol-lowering effect is an LDL cholesterol-lowering effect.

3. A pharmaceutical composition having a cholesterol lowering effect which comprises:

(a) as the active ingredient p-[3-(4-acetyl-3-hydroxy-2-propylphenoxy-propoxy] phenylacetic acid or a pharmaceutically acceptable salt thereof, which binds directly to and activates a PPAR in an amount effective for lowering cholesterol level, and (b) a pharmaceutically acceptable carrier or diluent.

4. A method for identifying a compound having a cholesterol-lowering effect comprising measuring an effect of direct activation of peroxisome proliferator-activated receptor (PPAR) δ or an effect of direct activation of PPARδ and PPAR γ.

* * * * *